(12) United States Patent
Lau et al.

(10) Patent No.: US 12,188,066 B2
(45) Date of Patent: Jan. 7, 2025

(54) METHOD FOR RESOLVING OPTICAL ISOMER BY USING SUPERCRITICAL FLUID EXTRACTION TECHNOLOGY

(71) Applicant: Guang An Mojia Biotechnology Co., Ltd., Guang An (CN)

(72) Inventors: Man Kit Lau, Guang An (CN); Jinhuan Su, Guang An (CN); Ansen Chiew, Guang An (CN); Yan Chen, Guang An (CN); Congming Zeng, Guang An (CN)

(73) Assignee: Guang An Mojia Biotechnology Co., Ltd., Guang An (CN)

( * ) Notice: Subject to any disclaimer, the term of this patent is extended or adjusted under 35 U.S.C. 154(b) by 604 days.

(21) Appl. No.: 17/606,448

(22) PCT Filed: Apr. 23, 2020

(86) PCT No.: PCT/CN2020/086420
§ 371 (c)(1),
(2) Date: Oct. 25, 2021

(87) PCT Pub. No.: WO2020/216295
PCT Pub. Date: Oct. 29, 2020

(65) Prior Publication Data
US 2022/0195471 A1    Jun. 23, 2022

(30) Foreign Application Priority Data
Apr. 26, 2019   (CN) .......................... 201910343769.6

(51) Int. Cl.
*C12P 17/04*      (2006.01)
*B01D 11/04*     (2006.01)
*C07D 307/33*  (2006.01)

(52) U.S. Cl.
CPC .......... *C12P 17/04* (2013.01); *B01D 11/0403* (2013.01); *C07D 307/33* (2013.01); *C07B 2200/07* (2013.01); *C07B 2200/13* (2013.01)

(58) Field of Classification Search
CPC ....... C12P 41/005; C12P 17/04; C12P 301/00; C12Y 305/02006
See application file for complete search history.

(56) References Cited

U.S. PATENT DOCUMENTS

| | | | |
|---|---|---|---|
| 5,275,949 A | 1/1994 | Sakamoto et al. | |
| 5,403,898 A | 4/1995 | Bradshaw et al. | |

FOREIGN PATENT DOCUMENTS

| | | |
|---|---|---|
| CN | 1926429 A | 3/2007 |
| CN | 1935977 A | 3/2007 |
| CN | 108117532 A | 6/2018 |
| CN | 108911962 A | 11/2018 |

OTHER PUBLICATIONS

International Search Report of PCT Application No. PCT/CN2020/086420.
Gao, Lihong, "Resolution of Enantiomeric Drugs by Supercritical Fluid Extraction", Medicine & Public Health, Chinese Selected Doctoral Dissertations and Master's Theses Full-Text Databases, No. 01, ISSN: 1671-6779, p. 13, Jun. 15, 2002.
Yi, Xin, "Design of a Supercritical Fluid Extraction, Rectification, Chromatography Preparation Device and Its Application", China Master's Theses Full-Text Database, Engineering Science & Technology I, No. 03, pp. 5-8, Mar. 15, 2019.
The extended European search report of European application No. 20794526.2, issued on May 10, 2023.
Simandi, B. et al., "Separation of enantiomers by supercritical fluid extraction", The Journal of Supercritical Fluids, Jun. 15, 1998, vol. 13, No. 1-3, pp. 331-336.
Szekely, E. et al., "Application of supercritical fluid extraction for fractionation of enantiomers", The Journal of Supercritical Fluids, Sep. 1, 2004, vol. 31, No. 1, pp. 33-40.
Chi, Xiao-Feng et al., "Obtaining alantolactone and isoalantolactone from Inula racemose Hook.f. by optimized supercritical fluid extraction", Industrial Crops and Products, Nov. 4, 2015, vol. 79, pp. 63-39.
Kmecz, Ildiko et al., "Application of mixtures of tartaric acid derivatives in resolution via supercritical fluid extraction", Chirality, Mar. 7, 2007, vol. 19, No. 6, pp. 430-433.

*Primary Examiner* — Tekchand Saidha
(74) *Attorney, Agent, or Firm* — Jun He Law Offices P.C.; Zhaohui Wang

(57) ABSTRACT

Provided is a method for resolving an optical isomer from a racemate by using supercritical fluid extraction technology. The method is mainly applied to the separation of a product obtained after enzymatic resolution. Taking a preparation process of D-pantolactone as an example, the key point is to separate D-pantolactone and L-pantolactone from an enzymatic resolution liquid by means of supercritical fluid extraction.

11 Claims, No Drawings

METHOD FOR RESOLVING OPTICAL ISOMER BY USING SUPERCRITICAL FLUID EXTRACTION TECHNOLOGY

CROSS-REFERENCE TO RELATED APPLICATIONS

This application is a national stage application under 35 U.S.C. § 371 of International Application No. PCT/CN2020/086420, filed Apr. 23, 2020, which claims the benefit of priority to Chinese Application No. 201910343769.6, filed Apr. 26, 2019, the contents of each of which applications are incorporated herein by reference in their entireties.

FIELD OF THE INVENTION

The present disclosure relates to the biotechnical field, and in particular, to resolution of optical isomers from racemates by using biocatalytic technique and supercritical fluid extraction technique.

RELATED ART

Chirality is an essential attribute of nature, and many biological macromolecules and biologically active substances have chiral characteristics. Although the chemical compositions of two or more different configurations of a chiral substance are the same, the physiological activities are usually different. Usually only one configuration has the desired activity, and other configuration(s) has(ve) little or no effect, or may even have toxic side effects. For example, pantothenic acid is one of the B vitamins and a component of coenzyme A. It participates in metabolism of protein, fat, and sugar, and plays an important role in substance metabolism. Its active ingredient is dextrorotatory pantothenic acid (vitamin B5), which is D-configuration. However, because pantothenic acid is unstable, its commercial form is mainly calcium D-pantothenate.

Resolution is one of the main ways to obtain optically pure chiral compounds. Compared with conventional chemical resolution, enzymatic resolution does not require expensive resolution reagents, has mild reaction conditions, has good optical selectivity, is environmentally friendly, and can perform some reactions that cannot be performed by the chemical resolution. The enzymatic resolution has been increasingly popularized by scientific researchers from various countries due to its significant advantages, and there have been many successful industrialization cases.

For example, D-pantolactone is an important chiral intermediate to produce pantothenic acid series products such as calcium D-pantothenate, D-panthenol, and D-pantethine. At present, the industrial synthesis of D-pantolactone mostly uses a technical route that combining a chemical method with a hydrolase resolution method. That is, racemic DL-pantolactone is produced by the chemical method, and then is hydrolyzed and resolved with D-pantolactone hydrolase. L-pantolactone and unreacted D-pantolactone are first extracted from the supernatant after the resolution with an organic solvent, and the water phase (containing D-pantoic acid) is lactonized with acid and then extraction is performed with an organic solvent, and then the resulting product is desalted, decolorized, and refined by recrystallization. For example, CN1313402A discloses that DL-pantolactone is resolved by using free or immobilized cells, and then extraction is performed with dichloromethane, the water phase is acidified with hydrochloric acid, and then extraction is performed with dichloromethane, and the crude D-pantolactone obtained after solvent recovery is recrystallized in acetone/isopropyl ether to obtain qualified D-pantolactone. This process needs to be improved. For example, in the process of extracting and refining D-pantoic acid obtained by enzyme reaction, a large amount of organic solvents is used for extraction, which brings environmental and cost problems, and crude D-pantolactone needs to be recrystallized and refined, which has low yield and high cost.

The supercritical fluid extraction technique is a new extraction and separation technique. It uses supercritical fluid, which is a fluid under a thermodynamic state with the temperature higher than the critical temperature and the pressure higher than the critical pressure, as an extractant to dissolve and separate specific components from fluid or solid to achieve the goal of extraction.

SUMMARY OF THE INVENTION

The present disclosure provides a novel method for resolving an optical isomer. The method can remedy the defects of the existing chiral resolution process, and replaces a conventional organic solvent extraction process with a supercritical fluid extraction technique according to different physical properties (such as melting point, or boiling point) or chemical properties (such as polarity, or lipophilicity), thereby improving the yield and product quality of the product, reducing the production cost, and also reducing the use amount of organic solvents and therefore making the operation more environmentally friendly and safer.

The present disclosure provides a method for resolving an optical isomer from a racemate by using a supercritical fluid extraction technique, including:
  a) reacting a racemate in the presence of the catalyst to form a mixture comprising a first form of a first optical isomer and a second form of a second optical isomer;
  b) performing extraction with supercritical fluid on the mixture to allow the first form of the first optical isomer and the second form of the second optical isomer to be separated; and
  c) collecting the separated first form of the first optical isomer, and/or collecting the separated second form of the second optical isomer.

In the present disclosure, the "racemate" refers to a mixture of two or more optical isomers with different optical rotation properties. For example, a compound with one chirality center may have two optical isomers, one with a chirality center in the R configuration, and the other with a chirality center in the S configuration. For the compound, its racemate includes both optical isomers in the R configuration and the S configuration. In the racemate of the present disclosure, different optical isomers may exist in equal molar mass (that is, optical rotation properties are offset), or may exist in unequal molar mass.

The point where the liquid phase and gas phase of a substance are in equilibrium is referred to as a critical point. The temperature at the critical point is referred to as a critical temperature, and the pressure at the critical point is referred to as a critical pressure. Different substances have different pressures and temperatures at the critical point. For example, for $CO_2$, the critical temperature is 31.1° C., and the critical pressure is 7.2 MPa; and for ethane, the critical temperature is 32.2° C., and the critical pressure is 4.87 MPa. In the present disclosure, the "supercritical fluid" refers to a fluid that behaves as a hybrid between a gas and a liquid, which is under a temperature higher than a critical temperature and a pressure higher than a critical pressure. The supercritical fluid has dual properties and advantages of both the gas and the liquid, such as strong solubility, good diffusivity, and easy controllability.

In some embodiments, the racemate has a hydrolyzable functional group. The hydrolyzable functional group includes, for example, but not limited to, an ester bond or an amide bond, etc. In some embodiments, the functional group may be hydrolyzed to form an ionizable group. The ionizable group refers to a group that can be ionized in an aqueous solution, such as a carboxyl group, an amino group, etc. The ionizable group produces charged groups after ionization, such as a negatively charged carboxylate, a positively charged ammonia ion, etc. In some embodiments, the physical and/or chemical properties, such as the polarity increases, the lipophilicity decreases, or the boiling point increases, of the optical isomer change after a functional group is hydrolyzed. In some embodiments, the chirality center in the racemate may be located within the hydrolyzable functional group, or may be located near the hydrolyzable functional group, for example, on the atom adjacent to the hydrolyzable functional group, or at a position separated from the hydrolyzable functional group by 1, 2, or 3 atoms.

In the method of the present disclosure, the catalyst may specifically react with a specific optical isomer in the racemate (for example, hydrolyze the hydrolyzable functional group therein) to covert the optical isomer into a first form of a first optical isomer, but cannot react with other optical isomers in the racemate. In the present disclosure, the "first form of the first optical isomer" refers to an existing form of the first optical isomer produced through specifical catalysis by a catalyst in the racemate. In some embodiments, the first form of the first optical isomer may include ionizable groups, such as a carboxyl group, an amino group, etc. In some embodiments, the first form of the first optical isomer has an increased polarity compared with the first optical isomer before being catalyzed by the catalyst in the racemate. In some embodiments, the first form of the first optical isomer has a reduced polarity compared with the first optical isomer before being catalyzed by the catalyst in the racemate. In some embodiments, the first form of the first optical isomer has a reduced lipophilicity compared with the first optical isomer before being catalyzed by the catalyst in the racemate. In some embodiments, the first form of the first optical isomer has an increased lipophilicity compared with the first optical isomer before being catalyzed by the catalyst in the racemate. In some embodiments, the first form of the first optical isomer has an increased boiling point compared with the first optical isomer before being catalyzed by the catalyst in the racemate. In some embodiments, the first form of the first optical isomer has a reduced boiling point compared with the first optical isomer before being catalyzed by the catalyst in the racemate. In some embodiments, the catalyst may not catalyze the second optical isomer in the racemate to keep it in a second form. The "second form of the second optical isomer" in the present disclosure refers to the second optical isomer that is not catalyzed by the catalyst in the racemate. In some embodiments, the second form of the second optical isomer includes non-ionized groups, such as ester (for example, lactone in a racemate), amide, ether, etc.

In some embodiments, the racemate has a ring structure, and the hydrolyzable functional group is within the ring structure. For example, an exemplary ring structure is lactone or lactam. These ring functional groups may react to open the ring. In some embodiments, the ring structure in the second form of the second optical isomer is closed. In some embodiments, the ring structure is ring-opened in the first form of the first optical isomer. For example, the ring functional group undergoes a ring-opening reaction to form ionizable groups. Alternatively, in some embodiments, the ring structure is ring-opened in the second form of second optical isomer, and/or the ring structure in the first form of the first optical isomer is closed. The chirality center of a racemate with a ring structure may or may not be on a ring atom.

In some embodiments, the racemate is ester. An exemplary racemic ester includes methyl 3-cyclohexene-1-carboxylate. In some embodiments, the racemate is lactone. The lactone has an intramolecular ester bond (—C(O)O) formed by dehydration of carboxyl and hydroxyl groups in the molecular structure. The intramolecular ester bond is usually in the ring structure. Examples of lactone include, for example, racemic DL-pantolactone, β-butyrolactone, γ-butyrolactone, α-hydroxy-γ-butyrolactone, β-hydroxy-γ-butyrolactone, α-acetyl-γ-butyrolactone, n-butylphthalide, etc.

In some embodiments, the catalyst comprises an enzyme composition. In some embodiments, the enzyme composition comprises an enzyme that can specifically react with a certain optical isomer. For example, the enzyme specifically reacts with a D-configuration optical isomer, or specifically reacts with an L-configuration optical isomer. In some embodiments, the enzyme composition comprises an ester hydrolase. In some embodiments, the ester hydrolase specifically catalyzes D-configuration lactone. Examples of ester hydrolase include D-pantolactone hydrolase, Novozyme 435 lipase, β-butyrolactone hydrolase, γ-butyrolactone hydrolase, α-hydroxy-γ-butyrolactone hydrolase, β-hydroxy-γ-butyrolactone hydrolase, α-acetyl-γ-butyrolactone hydrolase, n-butylphthalide hydrolase, etc. For example, the D-pantolactone hydrolase can specifically hydrolyze D-configuration pantolactone in the racemate, so that the lactone structure thereof is hydrolyzed to form intramolecular independent carboxyl and hydroxyl groups into the first form of the first optical isomer, that is, D-pantoic acid. However, the D-pantolactone hydrolase cannot hydrolyze L-configuration pantolactone in the racemate, so that the L-configuration pantolactone still remains the lactone structure after a catalytic reaction, which is the second form of the second optical isomer, that is, L-pantolactone. In another example, the Novozyme 435 lipase can specifically hydrolyze R-configuration methyl 3-cyclohexene-1-carboxylate in the racemate to form the first form of the first optical isomer, that is, 3-cyclohexene-1-carboxylic acid. S-configuration methyl 3-cyclohexene-1-carboxylate cannot be hydrolyzed, so that it still remains its configuration and structure to form the second form of the second optical isomer.

In some embodiments, the enzyme composition comprises lactamase. In some embodiments, the lactamase specifically catalyzes D-configuration lactam. Examples of lactamase includes, for example, β-lactamase or γ-lactamase. For example, the β-lactamase can specifically hydrolyze D-configuration β-lactam in the racemate, so that the lactam structure thereof is hydrolyzed to form intramolecular independent carboxyl and amino groups into the first form of the first optical isomer. However, the β-lactamase cannot hydrolyze L-configuration β-lactam in the racemate, so that the L-configuration β-lactam still remains the lactam structure after a catalytic reaction, which is the second form of the second optical isomer.

In some embodiments, in the present disclosure, the racemate is DL-pantolactone, the first optical isomer is D-pantolactone, the second optical isomer is L-pantolactone, the first form of the first optical isomer is D-pantoic acid, and the second form of the second optical isomer is L-pantolactone.

In some embodiments, the racemate is methyl 3-cyclohexene-1-carboxylate, the first optical isomer is (R)-methyl 3-cyclohexene-1-carboxylate, the second optical isomer is (S)-methyl 3-cyclohexene-1-carboxylate, the first form of the first optical isomer is (R)-3-cyclohexene-1-carboxylic acid, and the second form of the second optical isomer is (S)-methyl 3-cyclohexene-1-carboxylate.

In some embodiments, the racemate is α-hydroxy-γ-butyrolactone, the first optical isomer is (R)-α-hydroxy-γ-butyrolactone, the second optical isomer is (S)-α-hydroxy-γ-butyrolactone, the first form of the first optical isomer is (R)-α-hydroxy-γ-butyric acid, and the second form of the second optical isomer is (S)-α-hydroxy-γ-butyrolactone.

In some embodiments, the racemate is β-hydroxy-γ-butyrolactone, the first optical isomer is (R)-β-hydroxy-γ-butyrolactone, the second optical isomer is (S)-β-hydroxy-γ-butyrolactone, the first form of the first optical isomer is (R)-β-hydroxy-γ-butyric acid, and the second form of the second optical isomer is (S)-β-hydroxy-γ-butyrolactone.

In some embodiments, the racemate is α-acetyl-γ-butyrolactone, the first optical isomer is (R)-α-acetyl-γ-butyrolactone, the second optical isomer is (S)-α-acetyl-γ-butyrolactone, the first form of the first optical isomer is (R)-α-acetyl-γ-butyric acid, and the second form of the second optical isomer is (S)-α-acetyl-γ-butyrolactone.

Any form of enzyme with a selective catalytic function for optical isomers may be used. In some embodiments, the enzyme composition may comprise purified enzyme, enzyme-expressing cells, or enzyme-expressing lysates. The cells expressing the enzyme may be any suitable host cells, which may be prokaryotic cells, for example, bacteria, or may be eukaryotic cells, such as yeast and animal cells. The lysates of cells may be any lysate components containing enzyme, for example, cell lysis solution. In some embodiments, the enzyme composition is immobilized on a substrate. A suitable substrate may include materials for immobilizing enzyme, such as magnetic microspheres and macroporous resins, or may include materials for immobilizing cells, such as calcium alginate and gels.

In some embodiments, in step a), the pH value is maintained within the range of 7.0-7.5 during reaction, for example, the pH value is maintained at 7.0, 7.1, 7.2, 7.3, 7.4, 7.5, or any value between any two of the foregoing values. In some embodiments, ammonia solution (for example, 15N $NH_3 \cdot H_2O$) is used for titration to maintain the pH value. In some embodiments, sodium hydroxide (NaOH) solution is used for titration to maintain the pH value. In some embodiments, in step a), the temperature is maintained between 20° C. and 40° C. during reaction, for example, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or any value between any two of the foregoing values. In some embodiments, in step a), the reaction time is 1-10 h, for example, 1 h, 2 h, 3 h, 4 h, 5 h, 6 h, 7 h, 8 h, 9 h, 10 h, or any value between any two of the foregoing values.

In some embodiments, after step a) and before step b), the method further comprises removing a residue of the catalyst in the mixture. The residue includes macromolecules such as cell debris and proteins. A person skilled in the art may remove the residue of the catalyst in the mixture according to actual needs by using conventional separation methods, for example, one or more of a plurality of methods such as filtration, centrifugation, microfiltration, and ultrafiltration.

In some embodiments, the filtration is performed by using filter paper or filter cloth. The filter paper or filter cloth in the present disclosure could be commercially available filter paper or filter cloth, for example, filter paper or filter cloth produced by companies such as GE Healthcare Life Sciences, Spectrum Laboratories Inc., and Asahi KASEI. In some embodiments, the pore size of the filter paper or filter cloth is 10-150 μm, for example, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, or any value between any two of the foregoing values. A person skilled in the art may select a suitable pore size of the filter paper or filter cloth to remove the residue of the catalyst according to the type and size of the residue of the catalyst.

In some embodiments, the centrifugation is performed by using a centrifugal separator. The centrifugal separator in the present disclosure could be a commercially available centrifugal separator, for example, a centrifugal separator produced by companies such as Guangzhou Fuyi Liquid Separation Technology Co., Ltd., Yantai Chengbo Machinery Technology Co., Ltd., Dongguan Yaotian Electric Technology Co., Ltd., TEMA System, Kyte, Heinkel, and GEA. In some embodiments, the centrifugal rate is 1000-2000 rpm, for example, 1000 rpm, 1100 rpm, 1200 rpm, 1300 rpm, 1400 rpm, 1500 rpm, 1600 rpm, 1700 rpm, 1800 rpm, 1900 rpm, 2000 rpm, or any value between any two of the foregoing values. In some embodiments, the centrifugal time is 2-15 min, for example, 2 min, 3 min, 4 min, 5 min, 6 min, 7 min, 8 min, 9 min, 10 min, 11 min, 12 min, 13 min, 14 min, 15 min, or any value between any two of the foregoing values. A person skilled in the art may select a suitable centrifugal rate and centrifugal time to remove the residue of the catalyst according to the type and size of the residue of the catalyst.

In some embodiments, the microfiltration is performed by passing the mixture through a microfiltration membrane. The microfiltration membrane in the present disclosure could be a commercially available microfiltration membrane, for example, a hollow fiber microfiltration membrane series produced by companies such as GE Healthcare Life Sciences, Spectrum Laboratories Inc., and Asahi KASEI. In some embodiments, the pore size of the microfiltration membrane is 0.1-0.6 μm, for example, 0.1 μm, 0.15 μm, 0.2 μm, 0.22 μm, 0.25 μm, 0.3 μm, 0.35 μm, 0.4 μm, 0.45 μm, 0.5 μm, 0.55 μm, 0.6 μm, or any value between any two of the foregoing values. According to the size of the residue of the catalyst, selecting the pore size as small as possible of the microfiltration membrane helps to remove large-particle residues.

In some embodiments, the ultrafiltration is performed by passing the mixture through an ultrafiltration membrane. The ultrafiltration membrane in the present disclosure could be a commercially available ultrafiltration membrane, for example, a hollow fiber ultrafiltration membrane series produced by companies such as GE Healthcare Life Sciences, Spectrum Laboratories Inc., and Asahi KASEI. In some embodiments, the ultrafiltration membrane is a hollow fiber ultrafiltration membrane with a pore size of 10-500 kD, for example, a hollow fiber ultrafiltration membrane with a pore size of 10 kD, 20 kD, 30 kD, 40 kD, 50 kD, 60 kD, 70 kD, 80 kD, 90 kD, 100 kD, 150 kD, 200 kD, 250 kD, 300 kD, 350 kD, 400 kD, 450 kD, 500 kD, or any value between any two of the foregoing values. A person skilled in the art may select a suitable pore size of the ultrafiltration membrane to remove the residue of the catalyst according to the size of the residue of the catalyst.

In some embodiments, the method of the present disclosure further comprises purifying and/or concentrating the separated first form of the first optical isomer, and/or purifying and/or concentrating the separated second form of the second optical isomer.

In some embodiments, the separated first form of the first optical isomer and/or second form of the second optical isomer may be further purified. For example, the first form of the first optical isomer and/or the second form of the second optical isomer may be extracted by using a suitable solvent. For example, an organic solvent (for example, ethyl acetate) may be added into the collected (R)-3-cyclohexene-1-carboxylic acid, and the organic phase may be collected, to obtain the purified (R)-3-cyclohexene-1-carboxylic acid. In another example, an organic solvent (for example, ethyl acetate) may be further added into the collected (S)-methyl 3-cyclohexene-1-carboxylate, and the organic phase may be collected, to obtain the purified (S)-methyl 3-cyclohexene-1-carboxylate.

In some embodiments, the separated and/or purified first form of the first optical isomer and/or second form of the second optical isomer may be further concentrated. In some embodiments, the concentration is performed by reducing pressure. For example, the separated and/or purified first form of the first optical isomer and/or the separated and/or purified second form of the second optical isomer are/is pumped into a concentration equipment for concentration under reduced pressure.

In some embodiments, the present disclosure further comprises converting the second form of the second optical isomer into the racemate. The second form of the second optical isomer could be the substance separated by the method provided in the present disclosure, or may be further purified, or may be further concentrated. For example, when the racemate is an ester, the separated second form (that is, the ester) of the second optical isomer may be racemized to obtain the racemate with different chiral isomers. By reconverting the resolved second optical isomer into the racemate, the chiral resolution may be further performed by the method provided in the present disclosure to obtain more first optical isomers.

In some embodiments, the present disclosure further includes converting the separated first form of the first optical isomer into the first optical isomer. In some embodiments, the separated (and/or purified or concentrated) first form of the first optical isomer may be further reacted to restore the ionizable groups therein to hydrolyzable functional groups. For example, in some embodiments, the separated first form of the first optical isomer is D-pantoic acid, which may be lactonized to obtain D-pantolactone, so that the ionizable group (i.e., carboxyl group) therein is restored to the hydrolyzable functional group (i.e., lactone).

A person skilled in the art may use known methods and equipment to perform the supercritical fluid extraction step in the method of the present disclosure. For the supercritical fluid extraction equipment and methods, refer to *Supercritical $CO_2$ Extraction Device* (JB\T20136-2011)/Pharmaceutical Machinery Industry Standard of the People's Republic of China, *Supercritical Fluid Extraction*/Chemical Industry Press, etc.

In some embodiments, the extraction with supercritical fluid is carried out in a supercritical fluid extraction system, and the supercritical fluid extraction system includes a vessel containing a fluid, a cooling system, a compression system, an extraction kettle, and a separation kettle. In some embodiments, the vessel containing a fluid is a steel cylinder. In the present disclosure, the supercritical fluid extraction system can be commercially available, for example, the supercritical fluid extraction system produced by Beijing Fanhua Supercritical Extraction Device Co., Ltd., Hai'an Hua'an Supercritical Device Co., Ltd., or the like. A person skilled in the art may perform each operation steps of the supercritical fluid extraction according to the operation manual or instruction manual of the commercially available supercritical fluid extraction system.

In some embodiments, the solubilities of the first form of the first optical isomer and the second form of the second optical isomer in the supercritical fluid are different under an extraction temperature and an extraction pressure.

In the present disclosure, the "extraction temperature" refers to the temperature kept in the extraction kettle of the supercritical fluid extraction system during the extraction. In some embodiments, the extraction temperature is 28-40° C., such as 28° C., 29° C., 30° C., 31° C., 32° C., 33° C., 34° C., 35° C., 36° C., 37° C., 38° C., 39° C., 40° C., or any value between the foregoing two values. Preferably, the extraction temperature is 30-35° C.

In the present disclosure, the "extraction pressure" refers to a pressure kept in the extraction kettle of the supercritical fluid extraction system during the extraction. In some embodiments, the extraction pressure is 28-50 MPa, such as 28 MPa, 29 MPa, 30 MPa, 31 MPa, 32 MPa, 33 MPa, 34 MPa, 35 MPa, 36 MPa, 37 MPa, 38 MPa, 39 MPa, 40 MPa, 45 MPa, 50 MPa, or any value between the foregoing two values. Preferably, the extraction pressure is 30-35 MPa.

However, without being bound by any theory, it is considered that each of the factors such as temperature, pressure, polarity, lipophilicity, boiling point, or molecular weight may affect the solubility of a substance in a supercritical fluid. In some embodiments, the polarity of the first form of the first optical isomer is greater than the polarity of the second form of the second optical isomer. In some embodiments, the polarity of the first form of the first optical isomer is less than the polarity of the second form of the second optical isomer. In some embodiments, the lipophilicity of the first form of the first optical isomer is less than the lipophilicity of the second form of the second optical isomer. In some embodiments, the lipophilicity of the first form of the first optical isomer is greater than the lipophilicity of the second form of the second optical isomer.

However, without being bound by any theory, it is considered that a substance with a lower polarity and a higher lipophilicity has a higher solubility in a supercritical fluid under the extraction temperature and the extraction pressure. In some embodiments, the solubility of the first form of the first optical isomer in the supercritical fluid is significantly less than the solubility of the second form of the second optical isomer in the supercritical fluid under the extraction temperature and the extraction pressure. For example, the solubility of the first form of the first optical isomer in the supercritical fluid is 1/10-1/500 of the solubility of the second form of the second optical isomer in the supercritical fluid, such as 1/10, 1/20, 1/30, 1/40, 1/50, 1/60, 1/70, 1/80, 1/90, 1/100, 1/200, 1/300, 1/400, or 1/500. In some embodiments, the solubility of the first form of the first optical isomer in the supercritical fluid is significantly greater than the solubility of the second form of the second optical isomer in the supercritical fluid under the extraction temperature and the extraction pressure. For example, the solubility of the first form of the first optical isomer in the supercritical fluid is 10-500 times of the solubility of the second form of the second optical isomer in the supercritical fluid, such as 10 times, 20 times, 30 times, 40 times, 50 times, 60 times, 70 times, 80 times, 90 times, 100 times, 200 times, 300 times, 400 times, or 500 times.

In some embodiments, under the extraction temperature and the extraction pressure, the first form of the first optical isomer is hardly soluble in the supercritical fluid, and the second form of the second optical isomer is extremely soluble in the supercritical fluid, so that the first form of the first optical isomer and the second form of the second optical isomer are separated. The "hardly soluble" in the present disclosure means that, under the extraction temperature and the extraction pressure, the solubility of a optical isomer in the supercritical fluid is less than 1 g/L, such as less than 0.9 g/L, less than 0.8 g/L, less than 0.7 g/L, less than 0.6 g/L, less than 0.5 g/L, less than 0.4 g/L, less than 0.3 g/L, less than 0.2 g/L, less than 0.1 g/L, less than 0.09 g/L, less than 0.08 g/L, less than 0.07 g/L, less than 0.06 g/L, less than 0.05 g/L, less than 0.04 g/L, less than 0.03 g/L, less than 0.02 g/L, less than 0.01 g/L, etc. The "extremely soluble" means that, under the extraction temperature and the extraction pressure, the solubility of a optical isomer in the supercritical fluid is greater than 2 g/L, such as greater than 3 g/L, greater than 4 g/L, greater than 5 g/L, greater than 6 g/L, greater than 7 g/L, greater than 8 g/L, greater than 9 g/L, greater than 10 g/L, greater than 20 g/L, greater than 30 g/L, greater than 40 g/L, greater than 50 g/L, greater than 60 g/L, greater than 70 g/L, greater than 80 g/L, greater than 90 g/L, greater than 100 g/L, etc. A person skilled in the art may calculate the concentration of the supercritical fluid and the solubility of the optical isomer in the supercritical fluid according to conventional technical means in the art, for example, the method disclosed in Span and Wagner (1996), *A new equation of state for carbon dioxide covering the fluid region from the triple point temperature to 1100K at pressures up to 800 MPa*, J. Phys. Chem. Ref. Data, 25, 1509-1596 (http://www.energy.psu.edu/tools/CO2-EOS/index.php).

In some embodiments, the extraction with supercritical fluid includes placing the mixture in the extraction kettle, allowing the fluid from the vessel to enter the cooling system and the compression system to form the supercritical fluid, allowing the supercritical fluid to enter the extraction kettle to be in contact with the mixture to undergo extraction under the extraction temperature and the extraction pressure, allowing an extracted component with the supercritical fluid to enter the separation kettle to be separated, and collecting the extracted component.

In some embodiments, the supercritical fluid is $CO_2$, $N_2O$, $SF_6$, ethane, heptane, $NH_3$, or a combination thereof. In some embodiments, the supercritical fluid is $CO_2$. In some embodiments, the flow rate of $CO_2$ is 10-30 kg/h, such as 10 kg/h, 15 kg/h, 20 kg/h, 25 kg/h, 26 kg/h, 27 kg/h, 28 kg/h, 29 kg/h, 30 kg/h, or any value between the foregoing two values.

In some embodiments, an extraction time is 1-6 h, such as 1 h, 2 h, 3 h, 4 h, 5 h, 6 h, or any value between the foregoing two values.

In some embodiments, the separation kettle includes separation kettles in series. In some embodiments, the separation kettle includes three-stage separation kettles in series, wherein for a first-stage separation kettle, the separation temperature is 35-40° C. and the separation pressure is 7-9 MPa; for a second-stage separation kettle, the separation temperature is 25-28° C. and the separation pressure is 3-5 MPa; and for a third-stage separation kettle, the separation temperature is 45-48° C. and the separation pressure is 3-5 MPa. In some embodiments, the separation kettle includes separation kettles in series. In some embodiments, the separation kettle includes three-stage separation kettles in series, wherein for a first-stage separation kettle, the separation temperature is 40° C. and the separation pressure is 9 MPa; for a second-stage separation kettle, the separation temperature is 28° C. and the separation pressure is 5 MPa; and for a third-stage separation kettle, the separation temperature is 48° C. and the separation pressure is 51V1 Pa.

Racemic DL-pantolactone is used as an example. D-pantolactone hydrolase is added into a racemate to form a mixture of D-pantoic acid and L-pantolactone, the mixture is placed in an extraction kettle of a supercritical fluid extraction system, and then a formed supercritical fluid (for example, $CO_2$) enters the extraction kettle to be in contact with the mixture to undergo extraction under an extraction temperature and an extraction pressure for a certain time. The L-pantolactone is soluble in the supercritical fluid, but the D-pantoic acid is not soluble in the supercritical fluid. Therefore, the L-pantolactone with the supercritical fluid enters a separation kettle, while the D-pantoic acid remains in the extraction kettle and is lactonized with the addition of acid, to form D-pantolactone. The supercritical fluid with the L-pantolactone enters the separation kettle and undergoes multi-stage cooling and depressuring to gasify $CO_2$, and the extracted L-pantolactone is collected from the separation kettle, thereby achieving the resolution of D-type and L-type pantolactone.

In the method of the present disclosure, the inventors skillfully adjust and control the extraction temperature (for example, 28-40° C.), the extraction pressure (for example, 28-50 MPa), extraction time (for example, 1-6 h) and the parameters of temperature, pressure, etc. of the separation kettle, so as to ensure that the extraction in the extraction kettle is complete and $CO_2$ in the separation kettle is completely gasified and separated from the extract.

The purity of the optical isomer obtained through resolution by the method of the present disclosure is greater than 90%, for example, greater than 91%, 92%, 93%, 94%, 95%, 96%, 97%, 98%, or 99%, or even 100%. In some embodiments, the purity of the optical isomer obtained through resolution by the method of the present disclosure is represented by an ee value. A person skilled in the art may measure or calculate the ee value according to conventional technical means (for example, the HPLC method) in the art. For example, if a racemate contains two optical isomers A and B, ee value=A %–B %.

Compared with the related art, the present disclosure at least has the following advantages:

1. One of the advantages of the present disclosure is combining the biocatalysis (for example, enzyme catalysis) technique with the supercritical fluid extraction technique, and resolving the optical isomer in the racemate by using the supercritical fluid extraction technique according to different properties (such as polarity, lipophilicity, and boiling point) of the product produced by the enzyme catalysis, which has mild reaction conditions and reduces the operation steps.
2. The supercritical fluid extraction technique replaces conventional extraction methods, for example, conventional organic solvent extraction, which greatly reduces the amount of an organic solvent, reduces production costs, and reduces environmental pollution.
3. The present disclosure improves the extraction rate of the product, has good product purity so the product can be directly applied without further refining, reduces procedures, and has more cost advantages.

4. The process is simple and easy to implement, which facilitates automatic operation, improves the operation safety index, and improves the working environment of workers.

EXAMPLES

The present disclosure is further described below with reference to specific examples, but the protection scope of the present disclosure is not limited thereto.

Example 1

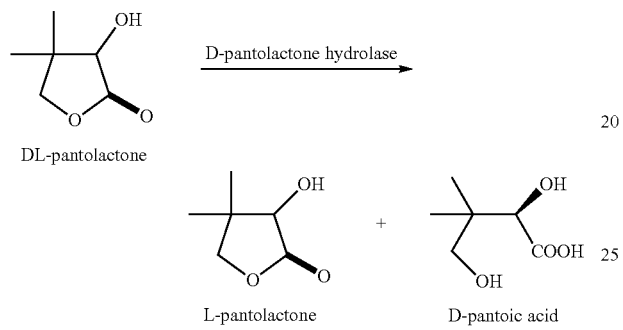

DL-pantolactone

L-pantolactone         D-pantoic acid

1. Preparation of an enzymatic conversion solution: 300 g of racemic DL-pantolactone and 150 g of immobilized cells containing D-pantolactone hydrolase were added into a 1 L system at 30° C. with a pH of 7.0, the mixture was mechanically stirred at 200 rpm, and was titrated with 15N $NH_3 \cdot H_2O$ to keep the pH value at 7.0, to react for 3 h.
2. Pretreatment of the enzymatic conversion solution: the enzymatic conversion solution was first filtered with a filter cloth, then filtered with a 0.2 μm microfiltration membrane, and then filtered with a 50 kD ultrafiltration membrane.
3. Supercritical fluid extraction: the filtered reaction liquid was poured into an extraction kettle of a supercritical fluid extraction system, the temperature of the extraction kettle was increased to 40° C., a supercritical fluid $CO_2$ was introduced and the flow rate was adjusted to 20 kg/h, and the pressure was increased to 35 MPa, to perform the extraction for 2 h; and the extracted L-pantolactone with $CO_2$ entered three-stage separation kettles in series (wherein for a first-stage separation kettle, the separation temperature was 40° C., and the separation pressure was 9 MPa; for a second-stage separation kettle, the separation temperature was 28° C., and the separation pressure was 5 MPa; and for a third-stage separation kettle, the separation temperature was 48° C., and the separation pressure was 5 MPa) for separation.
4. Concentration and acidification: a supernatant removed from the extraction kettle was injected into a concentration equipment to be concentrated to about 200 mL under reduced pressure, and sulfuric acid was added into the concentrated supernatant to about pH 1 to lactonize it.
5. Crystallization: after the concentration, an upper layer of the acidified solution was removed to obtain 123.9 g of D-pantolactone with a yield of 41.3% (based on DL-pantolactone), and the ee value of the D-pantolactone measured by HPLC was 98.6%.

Example 2

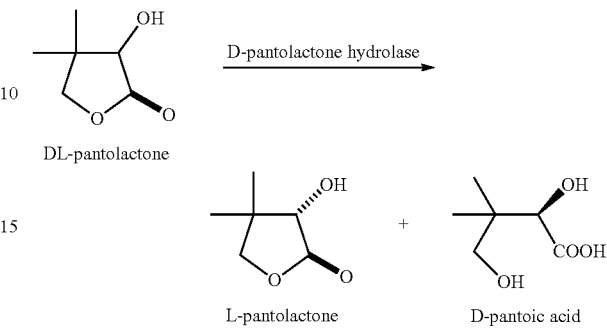

DL-pantolactone

L-pantolactone         D-pantoic acid

1. Preparation of an enzymatic conversion solution: 900 g of racemic DL-pantolactone and 450 g of immobilized cells containing D-pantolactone hydrolase were added into a 3 L system at 30° C. with a pH of 7.0, the mixture was mechanically stirred at 200 rpm, and was titrated with 15N $NH_3 \cdot H_2O$ to keep the pH value at 7.0, to react for 4 h.
2. Pretreatment of the enzymatic conversion solution: 3 L of the enzymatic conversion solution was filtered with a 0.4 μm microfiltration membrane, and then filtered with a 20 kD ultrafiltration membrane; and then the filtered supernatant was concentrated under reduced pressure to 500 mL.
3. Supercritical fluid extraction: the concentrate was poured into an extraction kettle of a supercritical fluid extraction system, the temperature of the extraction kettle was increased to 35° C., a supercritical fluid $CO_2$ was introduced and the flow rate was adjusted to 30 kg/h, and the pressure was increased to 35 MPa, to perform the extraction for 4 h; and the extracted L-pantolactone with $CO_2$ entered three-stage separation kettles in series (wherein for a first-stage separation kettle, the separation temperature was 40° C., and the separation pressure was 9 MPa; for a second-stage separation kettle, the separation temperature was 28° C., and the separation pressure was 5 MPa; and for a third-stage separation kettle, the separation temperature was 48° C., and the separation pressure was 5 MPa) for separation.
4. Concentration and acidification: sulfuric acid was added into a supernatant removed from the extraction kettle to about pH 1 to lactonize it.
5. Crystallization: after the concentration, an upper layer of the acidified solution was removed to obtain 364.5 g of D-pantolactone with a yield of 40.5% (based on DL-pantolactone), and the ee value of the D-pantolactone measured by HPLC was 96.6%.

Example 3

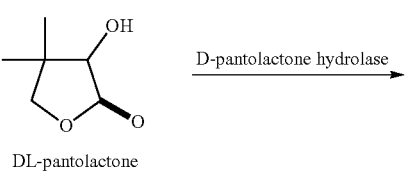

DL-pantolactone

-continued

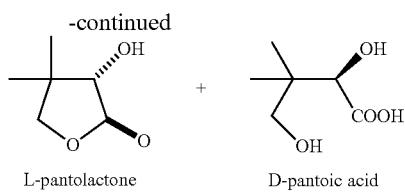

L-pantolactone    D-pantoic acid

1. Preparation of an enzymatic conversion solution: 900 g of racemic DL-pantolactone and 450 g of immobilized cells containing D-pantolactone hydrolase were added into a 3 L system at 30° C. with a pH of 7.0, the mixture was mechanically stirred at 200 rpm, and was titrated with 15N $NH_3 \cdot H_2O$ to keep the pH value at 7.0, to react for 4 h.
2. Pretreatment of the enzymatic conversion solution: 3 L of the enzymatic conversion solution was filtered with a 0.4 μm microfiltration membrane, and then filtered with a 20 kD ultrafiltration membrane.
3. Supercritical fluid extraction: the filtered reaction liquid was poured into an extraction kettle of a supercritical fluid extraction system, the temperature of the extraction kettle was increased to 40° C., a supercritical fluid $CO_2$ was introduced and the flow rate was adjusted to 20 kg/h, and the pressure was increased to 35 MPa, to perform the extraction for 6 h; and the extracted L-pantolactone with $CO_2$ entered three-stage separation kettles in series (wherein for a first-stage separation kettle, the separation temperature was 40° C., and the separation pressure was 9 MPa; for a second-stage separation kettle, the separation temperature was 28° C., and the separation pressure was 5 MPa; and for a third-stage separation kettle, the separation temperature was 48° C., and the separation pressure was 5 MPa) for separation.
4. Concentration and acidification: a supernatant removed from the extraction kettle was injected into a concentration equipment to be concentrated to about 500 mL under reduced pressure, and sulfuric acid was added into the concentrated supernatant to about pH1 to lactonize it.
5. Crystallization: after the concentration, an upper layer of the acidified solution was removed to obtain 388.8 g of D-pantolactone with a yield of 43.2% (based on DL-pantolactone), and the ee value of the D-pantolactone measured by HPLC was 98.9%.

The specific examples of the present disclosure are described above. It should be understood that the present disclosure is not limited to the foregoing specific embodiments, and a person skilled in the art may make various changes or modifications within the scope of the claims, which does not affect the essence of the present disclosure. The examples and the features in the examples of the present disclosure may be combined with each other randomly with no conflict.

What is claimed is:
1. A method for resolving an optical isomer from a racemate by using a supercritical fluid extraction technique, comprising:
 a) reacting the racemate in the presence of a catalyst to form a mixture comprising a first form of a first optical isomer and a second form of a second optical isomer;
 b) performing an extraction with supercritical fluid on the mixture to allow the first form of the first optical isomer and the second form of the second optical isomer to be separated; and
 c) collecting the separated first form of the first optical isomer, and/or collecting the separated second form of the second optical isomer,
wherein
the catalyst is an ester hydrolase and/or a lactamase;
 (1) the racemate is DL-pantolactone, the first form of the first optical isomer is D-pantoic acid, and the second form of the second optical isomer is L-pantolactone;
 (2) the racemate is methyl 3-cyclohexene-1-carboxylate, the first form of the first optical isomer is (R)-3-cyclohexene-1-carboxylic acid, and the second form of the second optical isomer is(S)-methyl 3-cyclohexene-1-carboxylate;
 (3) the racemate is α-hydroxy-γ-butyrolactone, the first form of the first optical isomer is (R)-α-hydroxy-γ-butyric acid, and the second form of the second optical isomer is(S)-α-hydroxy-γ-butyrolactone;
 (4) the racemate is β-hydroxy-γ-butyrolactone, the first form of the first optical isomer is (R)-β-hydroxy-γ-butyric acid, and the second form of the second optical isomer is(S)-β-hydroxy-γ-butyrolactone; or
 (5) the racemate is α-acetyl-γ-butyrolactone, the first form of the first optical isomer is (R)-α-acetyl-γ-butyric acid, and the second form of the second optical isomer is(S)-α-acetyl-γ-butyrolactone.
2. The method according to claim 1, further comprising purifying and/or concentrating the separated first form of the first optical isomer, and/or purifying and/or concentrating the separated second form of the second optical isomer.
3. The method according to claim 1, further comprising converting the second form of the second optical isomer into the racemate.
4. The method according to claim 1, wherein the extraction with supercritical fluid is carried out in a supercritical fluid extraction system, wherein the supercritical fluid extraction system comprises a vessel containing a fluid, a cooling system, a compression system, an extraction kettle, and a separation kettle.
5. The method according to claim 1, wherein the solubilities of the first form of the first optical isomer and the second form of the second optical isomer in a supercritical fluid are different under an extraction temperature and an extraction pressure.
6. The method according to claim 5, wherein the solubility of the first form of the first optical isomer in the supercritical fluid is significantly less than the solubility of the second form of the second optical isomer in the supercritical fluid.
7. The method according to claim 4, wherein the extraction with supercritical fluid comprises placing the mixture in the extraction kettle, allowing the fluid from the vessel to enter the cooling system and the compression system to form the supercritical fluid, allowing the supercritical fluid to enter the extraction kettle to be in contact with the mixture to undergo extraction under the extraction temperature and the extraction pressure, allowing an extracted component with the supercritical fluid to enter the separation kettle to be separated, and collecting the extracted component.
8. The method according to claim 4, wherein the supercritical fluid is $CO_2$, $N_2O$, $SF_6$, ethane, heptane, $NH_3$, or a combination thereof.
9. The method according to claim 8, wherein the supercritical fluid is $CO_2$.
10. The method according to claim 4, wherein the separation kettle comprises separation kettles in series.
11. The method according to claim 4, wherein the separation kettle comprises three-stage separation kettles in series, wherein for a first-stage separation kettle, the sepa- ration temperature is 35-40° C. and the separation pressure is 7-9 MPa; for a second-stage separation kettle, the separation temperature is 25-28° C. and the separation pressure is 3-5 MPa; and for a third-stage separation kettle, the separation temperature is 45-48° C. and the separation pressure is 3-5 MPa.

\* \* \* \* \*